United States Patent

Raml et al.

Patent Number: 5,206,420
Date of Patent: Apr. 27, 1993

[54] PROCESS FOR THE PREPARATION OF SUCCINYLCHOLINE HALIDES

[75] Inventors: Walter Raml, Hellmonsödt; Günther Eichberger, Weisskirchen, both of Austria

[73] Assignee: Hafslund Nycomed Pharma Aktiengesellschaft, Linz, Austria

[21] Appl. No.: 903,324

[22] Filed: Jun. 24, 1992

[30] Foreign Application Priority Data

Aug. 13, 1991 [AT] Austria ................................ 1591/91

[51] Int. Cl.⁵ ............................................. C07C 69/34
[52] U.S. Cl. .................................................. 560/196
[58] Field of Search ................................ 560/88, 196

[56] References Cited

PUBLICATIONS

Cheng-Hsia et al., *Bull. Inst. Chem., Acad. Sinica*, 26 47–54 (1979).
Chemical Abstracts 99:139354f (1983).
Phillips, *J.A.C.S.*, 71 3264 (1949).

Primary Examiner—José G. Dees
Assistant Examiner—Joseph M. Conrad
Attorney, Agent, or Firm—Wenderoth, Lind & Ponack

[57] ABSTRACT

Preparation of succinylcholine halides of formula I:

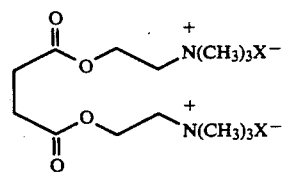

by reacting dialkyl succinates with an excess dimethylaminoethanol in the presence of an alkali metal alcoholate or alkali metal amide catalyst and then reacting the resulting bis(2-dimethylaminoethyl) succinates with methyl halides.

7 Claims, No Drawings

PROCESS FOR THE PREPARATION OF SUCCINYLCHOLINE HALIDES

The invention relates to a process for the preparation of succinylcholine halides.

Succinylcholine halides are pharmaceutically active compounds used as muscle relaxants.

Various processes for the preparation of succinylcholine halides are already known from the literature.

The Bulletin of the Institute of Chemistry, Academia Sinica, 26 (1979), pages 47–54, describes 5 methods for the preparation of succinylcholine chloride:

In method I succinic acid is reacted with dimethylaminoethanol to give bis(2-dimethylaminoethyl) succinate, which is then reacted with methyl chloride to give succinylcholine chloride.

Method II starts from bis(2-chloroethyl) succinate, which is reacted with dimethylamine. Succinylcholine chloride is then obtained by reaction with methyl chloride, as above.

However, the yield is relatively low for both methods.

Method III describes the reaction of succinic acid with ethylene chlorohydrin to give bis(2-chloroethyl) succinate, followed by alkylation with trimethylamine to give succinylcholine chloride, again only in low yield.

In method IV succinylcholine chloride is obtained by reacting succinyl dichloride with choline chloride. However, this method has the disadvantage that both the starting materials are very hygroscopic and hence are difficult to handle, and also that an additional step is required to prepare the acid chloride from succinic anhydride and thionyl chloride.

Method V starts from succinic anhydride, which is reacted in benzene with choline chloride in the presence of dry HCl as a catalyst. Here too it is necessary to use hygroscopic choline chloride. A further disadvantage is that of working with benzene.

J. Am. Chem. Soc. (1949) 149, page 3264, has disclosed a process for the preparation of bis($\beta$-dimethylaminoethyl) esters of aliphatic dicarboxylic acids by reacting the methyl or ethyl esters with a small excess of dimethylaminoethanol in the presence of small amounts of dissolved sodium. However, the desired amino esters are only obtained in low yields.

Unexpectedly a process for the preparation of succinylcholine halides has now been found in which succinylcholine halides are obtained in high yield and high purity starting from dialkyl succinates and dimethylaminoethanol, which acts simultaneously as a diluent, in the presence of an alkali metal alcoholate or alkali metal amide catalyst, and then reacting the products with methyl halides.

The invention accordingly relates to a process for the preparation of a succinylcholine halide of formula I:

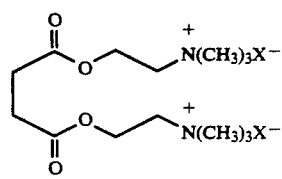

in which X is chlorine, bromine or iodine, characterized in that a dialkyl succinate of formula II:

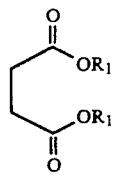

in which $R_1$ is $(C_1-C_4)$-alkyl, is treated with an excess of dimethylaminoethanol in the presence of alkali metal alcoholates or amides as a catalyst, the alcohol formed in the reaction being distilled off continuously, excess dimethylaminoethanol being recovered and the catalyst then being inactivated and filtered off, after which the resulting bis(2-dimethylaminoethyl) succinate of formula III:

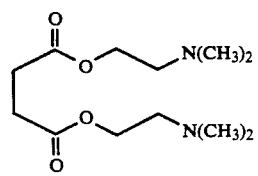

is reacted with methyl halides to give a compound of formula I.

The process according to the invention is carried out by first placing dimethylaminoethanol, which acts simultaneously as a diluent, in a reaction vessel flushed with $N_2$ and adding the catalyst all at once.

About 2.5 to 20 equivalents, i.e. 5 to 40 mol, of dimethylaminoethanol, preferably 7 to 10 mol and particularly preferably 8 to 9 mol, are used per mol of dialkyl succinate. The use of larger amounts of dimethylaminoethanol does not have any adverse effects on the reaction, although more dimethylaminoethanol has to be distilled off when the reaction has ended. The catalyst used consists of alkali metal alcoholates or amides, for example lithium methylate, lithium ethylate, lithium amide, sodium methylate, sodium amide, potassium amide or potassium methylate. It is preferable to use lithium methylate, lithium amide or sodium methylate. The amount of catalyst is about 0.5 to 6 percent by weight, based on dialkyl succinate, preferably about 1 to 3 percent by weight and particularly preferably about 2 percent by weight.

The mixture is then heated to about 30° to 120° C., preferably to about 75° to 90° C., and dialkyl succinate is added over a period of about 15 to 30 minutes. The dialkyl succinates used are esters having 1 to 4 C atoms, preferably 1 to 2 C atoms, in the alkyl chain. The reaction pressure can be between 50 and 760 mbar, preferably between 100 and 300 mbar. It is advantageous to lower the pressure, for example to 200 mbar, since the alcohol formed in the reaction can then be distilled off more easily and more rapidly.

The alcohol formed is distilled off continuously, the bulk of the alcohol being separated off within the first 15 to 30 minutes.

When the reaction has ended, the pressure is reduced further and excess dimethylaminoethanol is distilled off.

The dimethylaninoethanol recovered in this way can be reused as starting compound or as diluent. After the dimethylaminoethanol has been distilled off, the vacuum is let down to $N_2$ and the catalyst is inactivated, for example by adding an organic acid, e.g. acetic acid, oxalic acid, formic acid or succinic acid, to the reaction solution in an amount equivalent to the amount of catalyst.

To be able to filter off the resulting gelatinous precipitate more easily, the reaction mixture is preferably treated with an inert diluent which can easily be removed and recovered after the alkali metal salt formed has been filtered off. Diluents which can be used are inter alia benzines, toluene or ethers, e.g. diisopropyl ether. It is preferable to use diisopropyl ether. The remaining residue of bis(2-dimethylaminoethyl) succinate is then purified in conventional manner. Thin film evaporation and short path distillation are particularly suitable purification methods.

For further reaction the bis(2-dimethylaminoethyl) succinate is suspended in an inert diluent, e.g. acetone, tetrahydrofuran or diisopropyl ether, and clarified over activated charcoal if necessary. Acetone is preferably used as the diluent. A methyl halide is introduced into the suspension under pressure. 2 mol of methyl halide are required per mol of bis(2-dimethylaminoethyl) succinate. It is preferable to use 2.5 to 9 mol of methyl halide per mol of ester and particularly preferable to use 2.8 to 3.2 mol of methyl halide per mol of ester. The temperature is then raised to about 30° to 100° C., preferably to 40° to 60° C. When the reaction has ended, which is normally after about 1 to 20 hours, the reaction mixture is cooled and the diluent and excess methyl halide are distilled off. The recovered diluent and methyl halide can be reused as diluent and quaternizing agent respectively.

The succinylcholine halide obtained can be recrystallized in conventional manner, for example from an ethanol/water mixture.

Succinylcholine halides are obtained in high yields and in high purity by the process according to the invention.

EXAMPLE 1

Preparation of bis(2-dimethylaminoethyl) succinate 1418.56 g (15.9 mol) of dimethylaminoethanol were placed in a reaction vessel flushed with $N_2$, and 10 g (0.43 mol) of LiNH were added, NH then being evolved. The temperature was raised to approx. 70° C., the pressure was lowered to 200 mbar and 500 g (3.42 mol) of dimethyl succinate were added over 20 minutes. The methanol formed in the reaction was distilled off continuously, the bulk of the methanol (approx. 200 ml) being separated off in the first 15 minutes (theoretical total amount of methanol=277 ml).

After about 7 hours the pressure was lowered to 5 mbar and excess dimethylaminoethanol and residual methanol were distilled off. The vacuum was then let down to $N_2$ and the reaction mixture was treated with an equimolar amount of acetic acid, based on $LiNH_2$. To be able to filter off the resulting gelatinous precipitate of lithium acetate more easily, 2000 ml of diisopropyl ether were added to the reaction solution at approx. 50°–60° C.

The ether was then distilled from the filtrate and the remaining bis(2-dimethylaminoethyl) succinate was subjected to thin layer distillation.

Yield: 806 g (90.64%), purity: 99.5%

A number of other experiments were performed analogously. The data are shown in Table 1.

TABLE 1

|  | $LiOCH_3$ | $NaOCH_3$ | $KOCH_3$ |
|---|---|---|---|
| % by weight | 2 | 3 | 6 |
| T (°C.) | 65–87 | 65–80 | 65–88 |
| Crude yield | 96.6 | 87 | 99.9 |
| Purity after distillation | 99.5 | 99.2 | 99.5 |

EXAMPLE 2

Preparation of succinylcholine halide 54 g (0.21 mol) of bis(2-dimethylaminoethyl) succinate were dissolved in 700 ml of acetone, and 27 g (0.54 mol) of $CH_3Cl$ were introduced under pressure. After approx. 8 hours at 60° C. the reaction mixture was cooled and the acetone and excess $CH_3Cl$ were distilled off. The succinylcholine chloride obtained was recrystallized from an ethanol/$H_2O$ mixture (80/20).

Yield: 68 g (89.6%), white crystalline powder

Melting point: 160° C.

Purity: Content of choline chloride <0.5% Content of succinylmonocholine chloride <0.5%

What we claim is:

1. A process for the preparation of a succinylcholine halide of formula I:

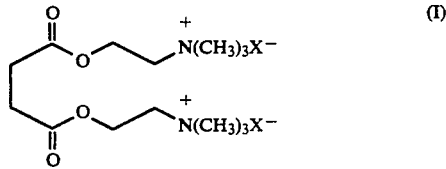
(I)

in which X is chlorine, bromine or iodine, characterized in that a dialkyl succinate of formula II:

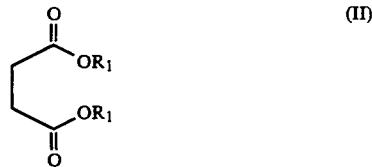
(II)

in which $R_1$ is $(C_1-C_4)$-alkyl, is treated with an excess of dimethylaminoethanol in the presence of alkali metal alcoholates or amides as a catalyst, the alcohol formed in the reaction being distilled off continuously, excess dimethylaminoethanol being recovered and the catalyst then being inactivated and filtered off, after which the resulting bis(2-dimethylaminoethyl) succinate of formula III:

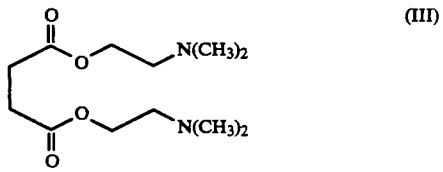
(III)

is reacted with methyl halides to give a compound of formula I.

2. A process according to claim 1, characterized in that lithium or sodium methylate is used as the catalyst.

3. A process according to claim 1, characterized in that lithium amide is used as the catalyst.

4. A process according to claim 1, characterized in that the amount of catalyst is 0.5 to 6% by weight, based on the starting compound of formula II, preferably 1 to 3% by weight.

5. A process according to clam 1, characterized in that the molar ratio of the compound of formula II to the dimethylaminoethanol is between 1:2.5 and 1:40, preferably between 1:7 and 1:10.

6. A process according to claim 1, characterized in that the reaction of dimethylaminoethanol with the compound of formula II is carried out at temperatures of 30° to 120° C., preferably of 75° to 90° C.

7. A process according to claim 1, characterized in that the catalyst is inactivated with an organic acid.

* * * * *

UNITED STATES PATENT AND TRADEMARK OFFICE
CERTIFICATE OF CORRECTION

PATENT NO. : 5,206,420

DATED : April 27, 1993

INVENTOR(S) : Walter RAML

It is certified that error appears in the above-identified patent and that said Letters Patent is hereby corrected as shown below:

Column 3, line 53, change "5 mbar" to --15 mbar--.

Signed and Sealed this

Eighteenth Day of January, 1994

*Attest:*

BRUCE LEHMAN

*Attesting Officer*     *Commissioner of Patents and Trademarks*